(12) United States Patent
Bunyan et al.

(10) Patent No.: US 9,333,366 B2
(45) Date of Patent: May 10, 2016

(54) CONSTRUCTION FOR AN IMPLANTABLE MEDICAL DEVICE HAVING A BATTERY AFFIXED TO THE CASE

(71) Applicant: Boston Scientific Neuromodulation Corporation, Valencia, CA (US)

(72) Inventors: Navin N. Bunyan, Valencia, CA (US); Robert R. Tong, Valencia, CA (US); Kurt Douglas Hampton, North Hollywood, CA (US); Jeffrey Van Funderburk, Stevenson Ranch, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/469,872

(22) Filed: Aug. 27, 2014

(65) Prior Publication Data
US 2015/0066115 A1   Mar. 5, 2015

Related U.S. Application Data

(60) Provisional application No. 61/874,197, filed on Sep. 5, 2013.

(51) Int. Cl.
*A61N 1/375* (2006.01)
*A61N 1/372* (2006.01)
(Continued)

(52) U.S. Cl.
CPC .......... *A61N 1/3758* (2013.01); *A61N 1/36125* (2013.01); *A61N 1/3787* (2013.01); *A61N 1/37229* (2013.01); *A61N 1/3754* (2013.01)

(58) Field of Classification Search
CPC   A61N 1/3758; A61N 1/36125; A61N 1/3787

USPC .......................................................... 607/36
See application file for complete search history.

(56) References Cited

U.S. PATENT DOCUMENTS 3,888,260 A   6/1975   Fischell
4,254,775 A   3/1981   Langer
(Continued)

FOREIGN PATENT DOCUMENTS

EP   0534782   3/1993
WO   2013/119439 A1   8/2013

OTHER PUBLICATIONS

International Search Report and Written Opinion regarding corresponding PCT Application No. PCT/US2014/053305, dated Oct. 24, 2014.

*Primary Examiner* — Carl H Layno
*Assistant Examiner* — Jennifer Ghand
(74) *Attorney, Agent, or Firm* — Lewis, Reese & Nesmith, PLLC

(57) ABSTRACT

Designs and methods of construction for an implantable medical device employ an internal support structure. The single-piece support structure holds various electronic components such as a communication coil and a circuit board, and further is affixed to a battery, thus providing a subassembly that is mechanically robust. The support structure further provides electrical isolation between these and other components. A method of construction allows for the subassembly to be adhered to a case of the implantable medical device at the battery, and possibly also at the support structure. The battery includes an insulating cover having holes. An adhesive is used consistent with the location of the holes to affix the battery to the case without electrically shorting the battery to the case.

28 Claims, 10 Drawing Sheets

(51) Int. Cl.
*A61N 1/378* (2006.01)
*A61N 1/36* (2006.01)

(56) References Cited

U.S. PATENT DOCUMENTS

| | | | |
|---|---|---|---|
| 4,314,562 A | 2/1982 | Ware | |
| 4,399,819 A | 8/1983 | Cowdery | |
| 4,441,498 A | 4/1984 | Nordling | |
| 4,741,710 A | 5/1988 | Hogan et al. | |
| 5,103,818 A | 4/1992 | Maston et al. | |
| 5,131,388 A | 7/1992 | Pless et al. | |
| 5,144,946 A | 9/1992 | Weinberg et al. | |
| 5,207,218 A | 5/1993 | Carpentier et al. | |
| 5,370,669 A | 12/1994 | Daglow et al. | |
| 5,405,363 A | 4/1995 | Kroll et al. | |
| 5,431,695 A | 7/1995 | Wiklund et al. | |
| 5,456,698 A | 10/1995 | Byland et al. | |
| 5,535,097 A | 7/1996 | Ruben et al. | |
| 5,741,313 A | 4/1998 | Davis et al. | |
| 5,951,594 A | 9/1999 | Kerver | |
| 6,040,082 A | 3/2000 | Haas et al. | |
| 6,115,634 A | 9/2000 | Donders et al. | |
| 6,445,948 B1 | 9/2002 | Somdahl et al. | |
| 6,498,951 B1 | 12/2002 | Larson et al. | |
| 6,505,073 B2 | 1/2003 | Gramse | |
| 6,721,602 B2 | 4/2004 | Engmark et al. | |
| 6,799,072 B2 | 9/2004 | Ries et al. | |
| 6,931,284 B2 | 8/2005 | Engmark et al. | |
| 6,963,780 B2 | 11/2005 | Ruben et al. | |
| 7,123,966 B2 | 10/2006 | Deininger et al. | |
| 7,194,310 B2 | 3/2007 | Neumann et al. | |
| 7,263,401 B2 | 8/2007 | Scott et al. | |
| 7,713,656 B2 | 5/2010 | Zhao et al. | |
| 7,803,014 B2 | 9/2010 | Sprain et al. | |
| 8,041,427 B2 | 10/2011 | Kast et al. | |
| 8,082,037 B2 | 12/2011 | Deininger et al. | |
| 8,359,098 B2 | 1/2013 | Lund et al. | |
| 8,457,744 B2 | 6/2013 | Janzig et al. | |
| 2004/0082977 A1* | 4/2004 | Engmark et al. | 607/36 |
| 2004/0230250 A1* | 11/2004 | Neumann et al. | 607/36 |
| 2009/0018600 A1* | 1/2009 | Deininger et al. | 607/36 |

* cited by examiner

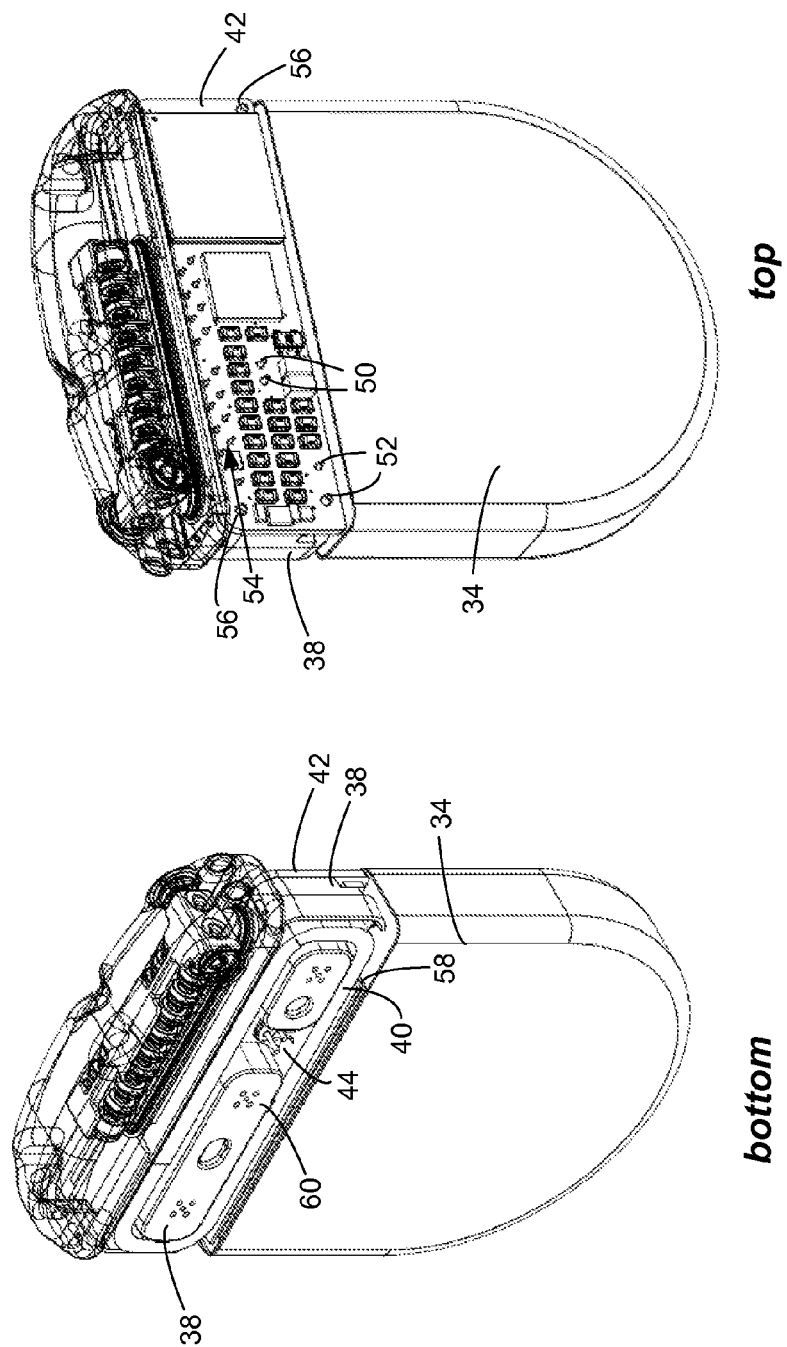

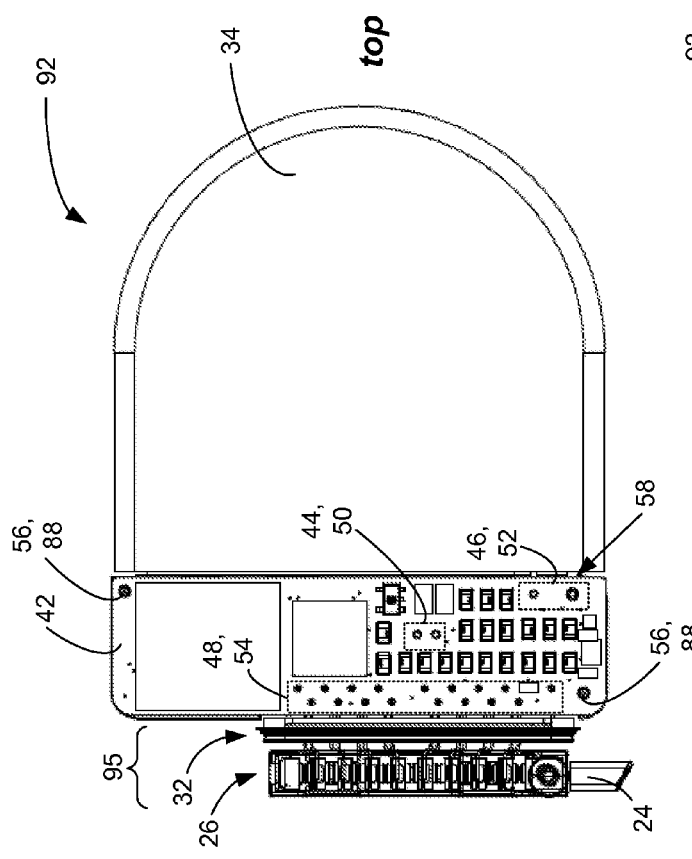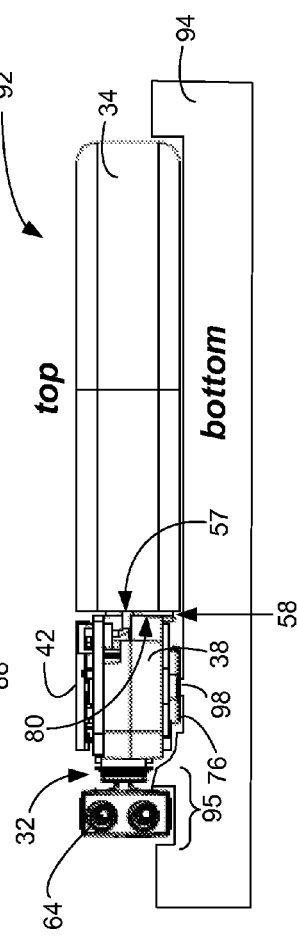

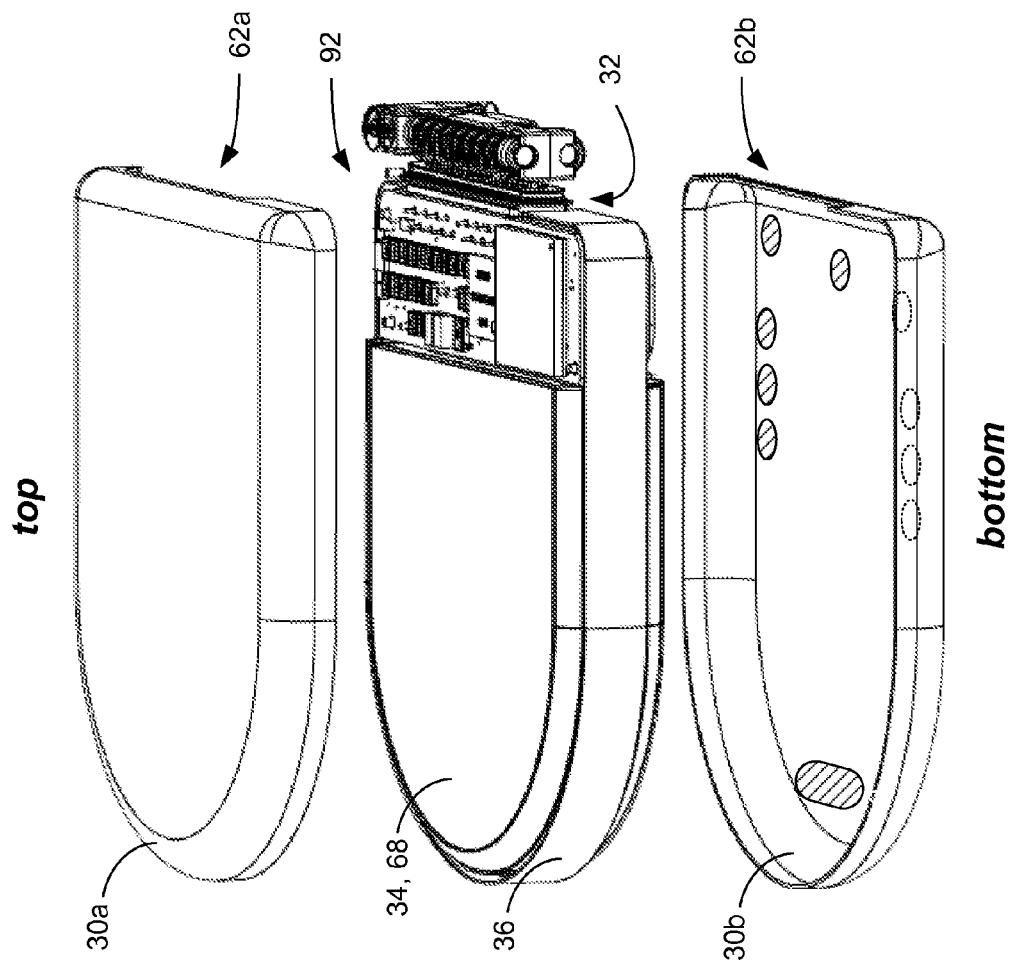

CONSTRUCTION FOR AN IMPLANTABLE MEDICAL DEVICE HAVING A BATTERY AFFIXED TO THE CASE

CROSS REFERENCE TO RELATED APPLICATIONS

This is a non-provisional of U.S. Provisional Patent Application Ser. No. 61/874,197, filed Sep. 5, 2013, which is incorporated herein by reference in its entirety, and to which priority is claimed.

This application is related to an application entitled "Construction for an Implantable Medical Device Employing an Internal Support Structure," Ser. No. 61/874,194, filed Sep. 5, 2013, which is incorporated herein by reference.

FIELD OF THE INVENTION

The present invention relates to implantable medical devices, and more particularly to an improved design and method of construction for an implantable medical device.

BACKGROUND

Implantable stimulation devices deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability with any implantable medical device or in any implantable medical device system.

A SCS system typically includes an Implantable Pulse Generator (IPG) which has a biocompatible device case formed of a conductive material such as titanium, for example. The case typically holds the circuitry of the IPG and a battery to provide power to the circuitry. Depending on the particular needs and circumstances of the patient who will be using the IPG, the battery can be either rechargeable or a non-rechargeable primary battery.

Although many IPGs use rechargeable batteries, there are situations in which use of a primary battery may be advantageous. A primary battery is one in which the electrochemical reaction is not reversible by passing a charging current therethrough, thus rendering the battery non-rechargeable. Primary batteries use up the materials in one or both of their electrodes and thus have a limited life span, but they are typically cheaper than rechargeable batteries, and may not suffer from the same reliability concerns. As such, the use of primary batteries in a medical implantable device is preferred when appropriate, for example, when the expected life of the primary battery would be expected to exceed the patient's life expectancy, or in situations where patients with physical or mental limitations would have difficulty charging the battery. Use of a primary battery in an IPG, however, creates a challenge in the design and construction of the IPG, as a primary battery is generally larger in size than a rechargeable one, and it is not optimal to increase the size of the IPG.

BRIEF DESCRIPTION OF THE DRAWINGS

FIG. 3 shows bottom and top perspective views of the improved IPG with its case removed.

FIGS. 6A and 6B respectively show top and cross-sectional views of a subassembly of the improved IPG at one stage of its construction.

FIG. 9 shows affixing the subassembly to the case portion using the glue drops, and encompassing the subassembly in the IPG case, at another stage of construction.

DETAILED DESCRIPTION

This disclosure provides an improved design and method of construction for an implantable medical device, and in particular an implantable medical device having a larger primary battery. However, the design and method of construction are not limited to implantable medical devices that use primary batteries, and can be used with rechargeable-battery IPGs as well. This improved design is easy to construct, mechanically robust, and uses few parts.

Figure 1:
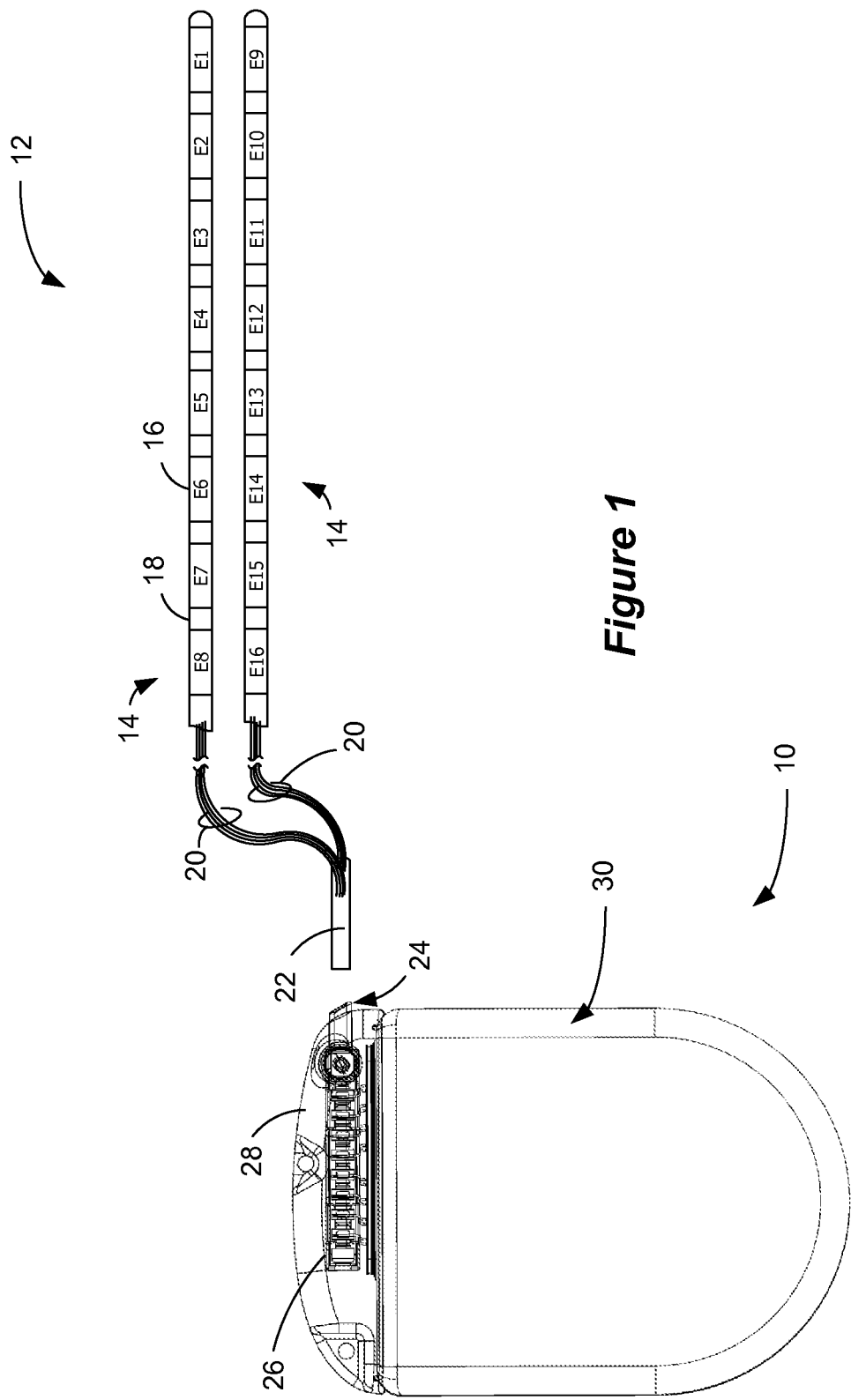
FIG. 1 shows an improved Implantable Pulse Generator (IPG) and the manner in which electrode leads are affixed to the IPG.
Figure 2:
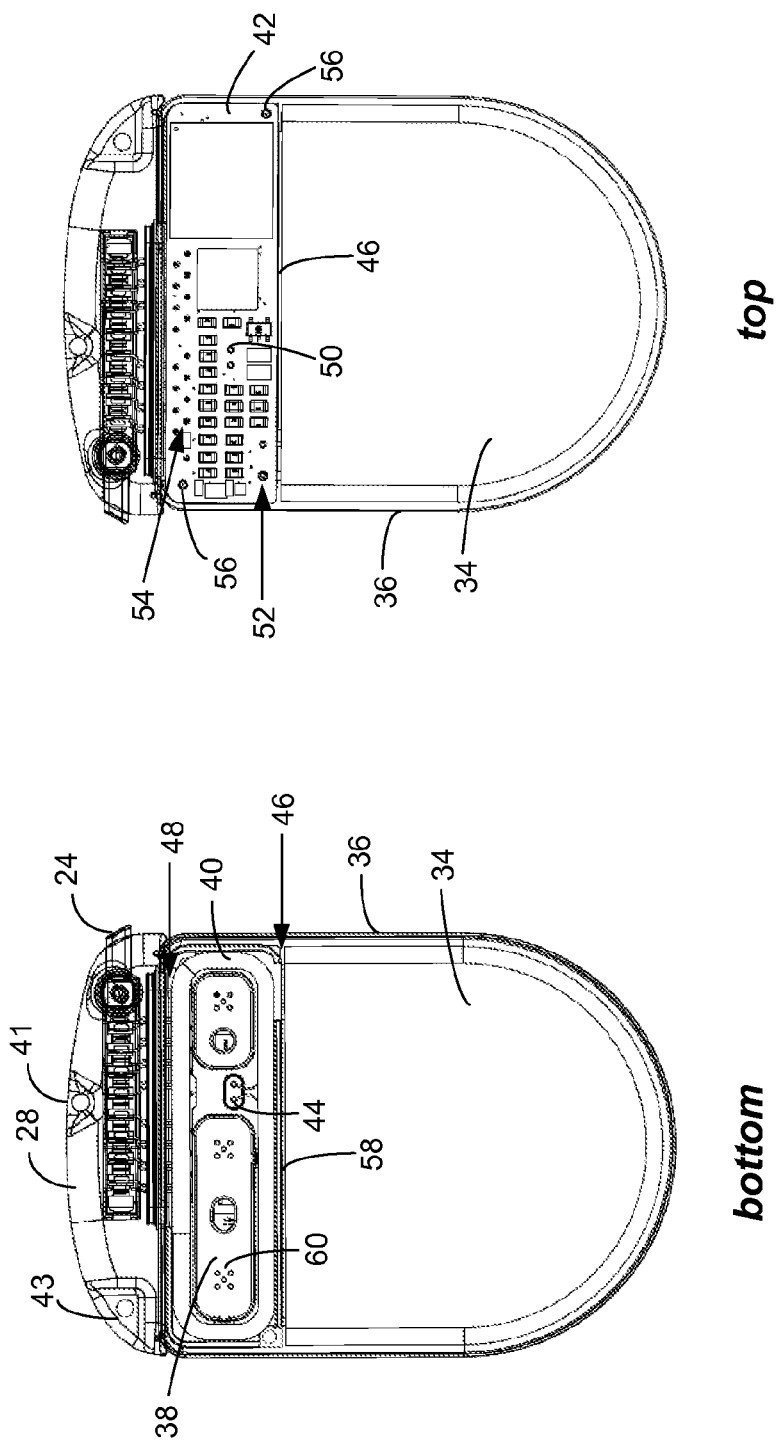
FIG. 2 shows bottom and top views of the improved IPG with its case removed.

FIG. 1 shows a SCS system having an IPG 10. The IPG 10 includes a biocompatible device case 30 that holds the circuitry and battery 34 (FIG. 2) necessary for the IPG to function. The IPG 10 is coupled to electrodes 16 via one or more electrode leads 14 that form an electrode array 12. The electrodes 16 are carried on a flexible body 18, which also houses the individual signal wires 20 coupled to each electrode. The signal wires 20 are connected to the IPG 10 at one or more lead connectors 24 fixed in a header 28, which can comprise an epoxy for example. In the illustrated embodiment, there are sixteen electrodes split between two leads 14, although the number of leads and electrodes is application specific and therefore can vary. In a SCS application, electrode leads 14 are typically implanted on the right and left side of the dura within the patient's spinal cord. The proximal ends 22 of the leads 14 are then tunneled through the patient's flesh to a distant location, such as the buttocks, where the IPG case 30 is implanted, at which point they are coupled to the lead connector(s) 24.

FIGS. 2, 3, and 4A and 4B show various perspectives of the bottom side (the side proximate a communication coil 40) and top side (the side proximate to a printed circuit board (PCB) 42) of the improved IPG 10. The case 30, which in the depicted example is formed as two case portions 30a and 30b, is removed in FIGS. 2 and 3 so that certain internal components can be seen, some of which are introduced now prior to discussion of the construction of the IPG 10.

As shown, the majority of the room inside the case 30 is taken up by a battery 34 which, in this example, is a permanent, non-wirelessly-rechargeable battery. The remainder of the room in the case 30 is largely taken up by a support structure 38, communication antenna 40, which is this example comprises a coil, and a PCB 42. The communication coil 40 enables communication between the IPG 10 and a device external to the patient (not shown), thus allowing bidirectional communication to occur by magnetic induction. The PCB 42 includes circuitry configured to implement the functionality of the implantable medical device. The lead connectors 24 are coupled to the PCB 42 by feedthrough pins 48, which proceed through a feedthrough 32 that is ultimately welded to the case 30 prior to securing the header 28 to the IPG 10, as explained below. Suture holes 41 and 43 in the header are used to suture the IPG to a patient's body during an operation.

Figure 5:
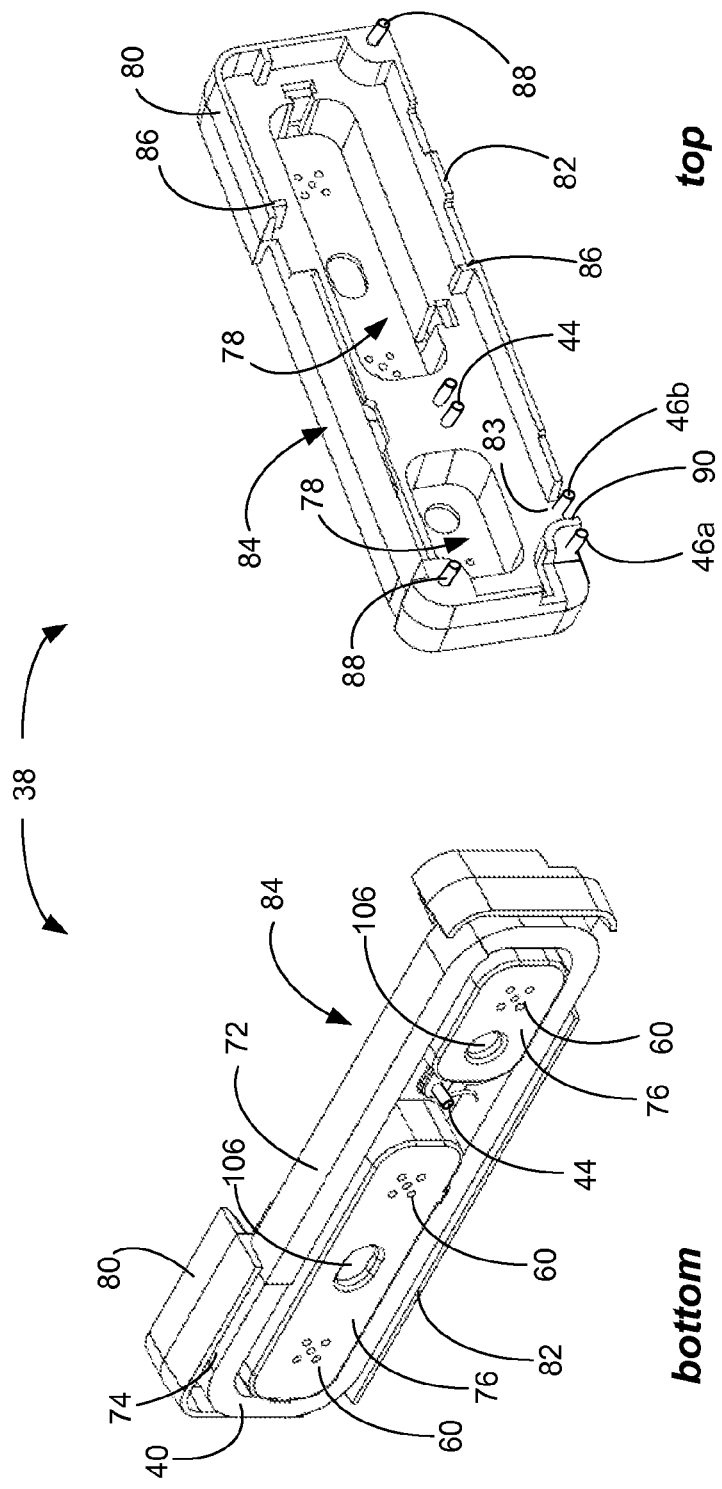
FIG. 5 shows bottom and top perspective views of a support structure used in the improved IPG.

Construction of the IPG 10 begins with the discussion of the support structure 38, which is shown in bottom and top perspective views in FIG. 5. The support structure 38 provides many benefits to the IPG 10. The support structure 38 comprises a single piece for receiving, holding, and protecting both the coil 40 and PCB 42. The coil 40, PCB 42, and battery 34 are affixed to the support structure 38, which integrates the connections of these components and results in a mechanically-robust IPG subassembly 92 (FIG. 6A) resistant to shock and vibration. Support structure 38 also provides electrical isolation between the coil 40 and the PCB 42 (excepting the coil pins 44 explained below); between the battery 34 (particularly, the positive terminal 46a of the battery 34) and the coil 40, PCB 42, or feedthrough pins 48; and between the feedthrough pins 48 and the coil 40, and thus prevents unwanted shorting of these components.

The support structure 38 also provides one or more case contact surfaces 76 with at least one glue hole 60 to allow the support structure 38, and hence the already-robust IPG subassembly 92, to be adhered to the case 30. The IPG subassembly 92 may additionally be adhered to the case 30 by the battery 34, as discussed below.

The support structure 38 includes a recess 74 into which the coil 40 is affixed. The coil 40 was earlier wound around a bobbin (not shown). The coil 40 is preferably recessed below the case contact surfaces 76 of the support structure 38 to protect it and to offset the coil 40 from the case 30 once the IPG 10 is constructed, as discussed further below. The ends of the coil 40 are soldered to coil pins 44 on the bottom side of the support structure 38, which coil pins 44 pass through the support structure 38 and are preferably molded into the support structure 38 during its construction. Later in the construction process, the other (top) side of coil pins 44 will be soldered to the PCB 42 on the top side of the support structure 38 to electrically couple the coil to the electronics on the PCB 42 such as modulation and/or demodulation circuitry. Coil 40 may be further affixed within the recess 74 using an epoxy or other adhesive. Coil 40 may be covered with tape 72 as shown to electrically isolate the coil 40 from the feedthrough pins 48, which later during construction will be located within a gap 84 in a sidewall 80 of the support structure 38.

The support structure 38 is preferably made of a material with high melting temperature able to withstand soldering of the coil pins 44 to the coil 40 and to other structures as subsequently explained. The material for the support structure 38 is also preferably mechanically rigid to provide mechanical robustness, and should have a low moisture content consistent with its use with electrical components and in an implantable medical device. In one embodiment, the material comprises a Liquid Crystal Polymer (LCP).

Several features of the support structure 38 that provide some of the benefits discussed earlier are noticeable in FIG. 5. For example, the top of the support structure 38 includes support ribs 86 and mounting pins 88 that help to support and position the PCB 42 that will be affixed to the support structure 38 later during construction. The support structure 38 also includes cavities 78, which provides space for taller components on the PCB 42. The cavities 78 also help to define the recess 74 for the coil 40, and provide two case contact surfaces 76 with glue holes 60 on the bottom side of the support structure 38, which as already noted is useful in adhering the support structure to the IPG's case 30. The sidewall 80 of the support structure 38 again helps to define the recess 74 and isolate the coil 40, and additionally comprises a portion 82 to which the battery 34 will be affixed, as explained later. An isolation structure 90 and gap 83 in the sidewall will accommodate the positive and negative terminals 46a and 46b of the battery 34 later during construction. Jig mounting holes 106 can also be seen on the bottom of the support structure 38, whose function is later explained.

After formation of the support structure 38, various pieces of the IPG 10—for example, the support structure 38, the PCB 42, the battery 34 and a lead connector subassembly 95 (explained below)—can be electrically and mechanically attached to form an IPG subassembly 92, as shown in top and cross-sectional views of FIGS. 6A and 6B.

Figure 4A:
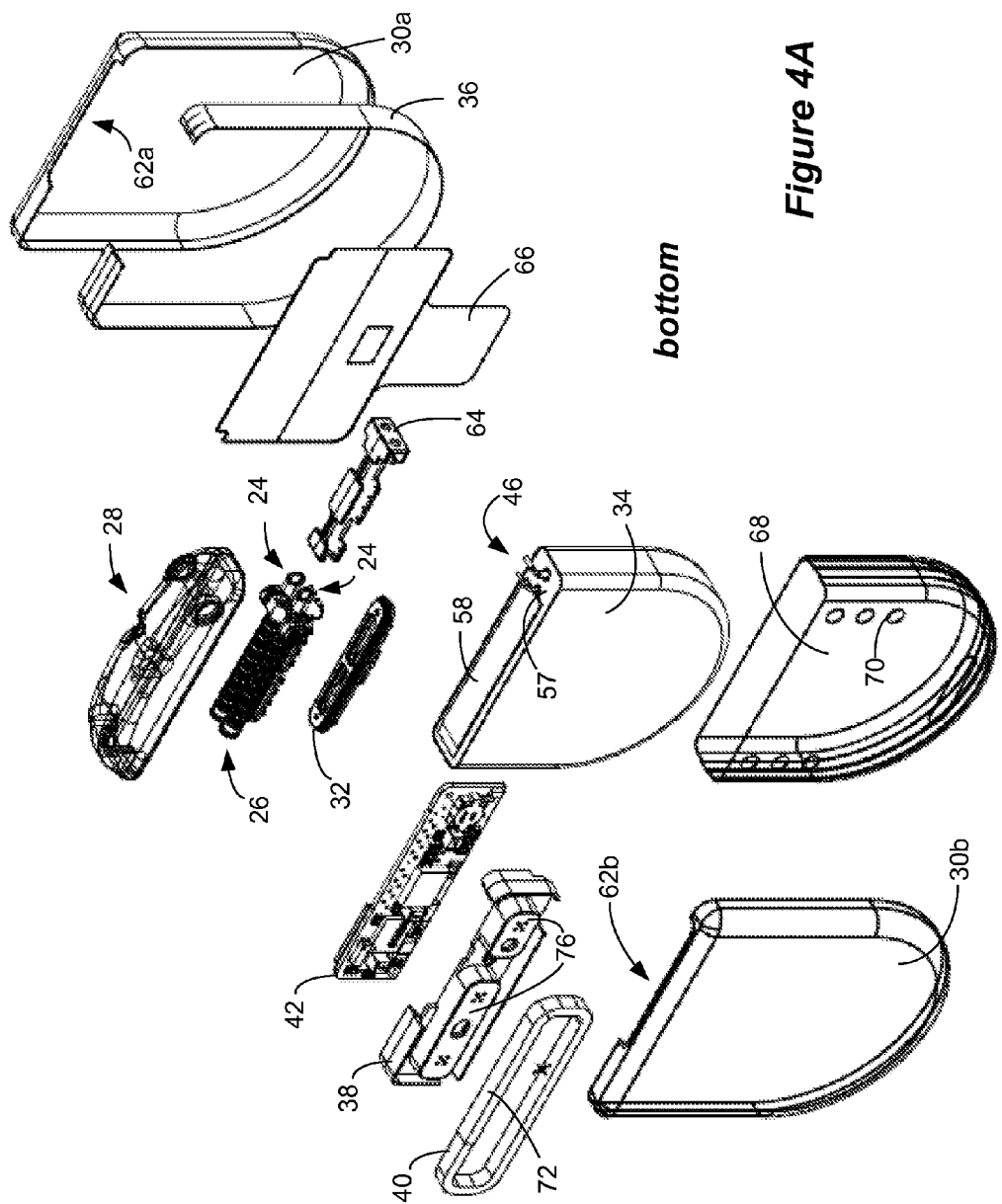
FIGS. 4A and 4B respectively show bottom and top perspective exploded views of the components of the improved IPG.
Figure 4B:
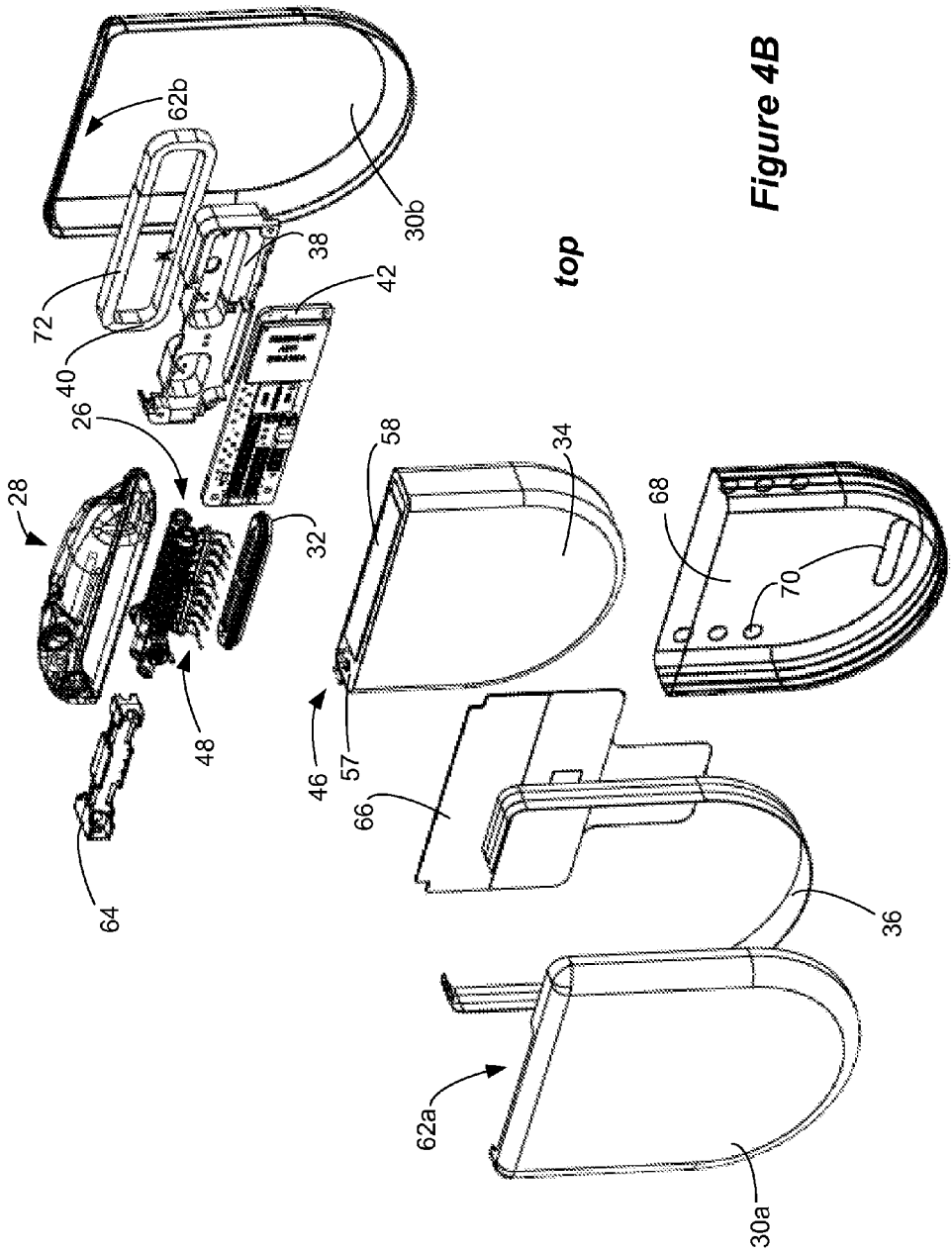

Construction begins by adhering double sided tape 58 to the face 57 of the battery 34 that contains the battery terminals (FIGS. 4A and 4B). The other side of the double sided tape 58 is adhered to the sidewall portion 82 of the support structure 38. As noted earlier, the support structure 38 preferably already contains the coil 40 pre-soldered to the coil pins 44, but the coil could also be affixed to the support structure at this time or later during construction, such as when soldering of components to the PCB 42 subsequently occurs. Because the case contact surfaces 76 on the bottom of the support structure 38 and the bottom surface of the battery 34 are preferably planar, support structure 38 and battery 34 can be affixed with the double sided tape 58 by sliding them together on a flat surface. It is not strictly necessary to use double sided tape 58 to affix the battery 34 to the support structure 38, and glue or other adhesives could be used as well.

The terminals 46a and 46b of the battery 34 are bent at 90 degrees relative to the flat battery terminal surface of the battery 34 and so are now pointing upward, as best shown in the top view of FIG. 5. Notice in FIG. 5 that the negative terminal 46b passes through the gap 83 in the sidewall 80 of the support structure 38, and that the positive terminal 46a of the battery 34 is at least partially surrounded by the isolation structure 90 formed in the support structure 38. As such, the support structure 38, in addition to other functions, serves to isolate the positive battery terminal 46a from shorting to the negative battery terminal 46b and other components in the IPG 10, such as the coil 40 and the PCB 42. Isolation structure 90 could be made in differing manners. The negative battery terminal 46b could also be isolated using an isolation structure 90.

Next, the combined support structure 38 and battery 34 is placed in an assembly jig 94 as shown in FIG. 6B, which has recesses conforming to the shape of these pieces it receives to align and hold them during construction. As shown, the jig 94 can have mounts 98 designed to mate with the jig mounting holes 106 on the bottom side of the support structure 38 to securely hold the combined support structure 38 and battery 34 in the jig 94. Other means of support with the jig 94 could be used as well.

Next, a lead connector subassembly 95 is positioned within the jig 94. The lead connector subassembly 95 includes the lead connectors 24, the electrode contacts 26, a carrier 64 (used to house and support the electrode contacts 26; see FIGS. 4A and 4B), the feedthrough pins 48, and the feedthrough 32, and may be pre-formed prior to this step in construction. For example, lead connector subassembly 95 can be formed by slipping the feedthrough pins 48 through the feedthrough 32, soldering one end of the feedthrough pins 48 to appropriate electrode contacts 26 in the lead connectors 24, and (if necessary) soldering the feedthrough pins 48 in the feedthrough 32 in a hermetic manner. Notice that the free end of the feedthrough pins 48 are bent at 90 degrees relative to the feedthrough 32 (as best seen in FIG. 4B), and so when placed in the jig 94 are now pointing upward. Notice also that the feedthrough pins 48 will be positioned in the gap 84 in the sidewall 80 of the support structure 38 (FIG. 5), as discussed earlier.

Next, the PCB 42—preferably pre-fabricated with its electrical components—is affixed to the top side of the support structure 38. In this regard, PCB 42 includes coil solder pin holes 50, battery terminal solder holes 52, feedthrough pin solder holes 54, and support structure mounting holes 56, which are respectively slipped over and brought into contact with the upward-pointing coil pins 44, feedthrough pins 48, battery terminals 46a and 46b, and mounting pins 88 of the support structure 38. Once the PCB 42 is slid over these structures, it comes to rest on the support ribs 86 (FIG. 5), which provides suitable mechanical support to keep the PCB 42 from flexing. The coil pins 44, feedthrough pins 48, battery terminals 46a and 46b are then soldered to the coil solder pin holes 50, feedthrough pin solder holes 54, and battery terminal solder holes 52 respectively to electrically couple them to the PCB 42. The combined effect of the support ribs 86, mounting pins 88, and the soldered connections yields a PCB 42 that is firmly affixed to and protected by the support structure 38 to complete the IPG subassembly 92. Although not shown, the PCB 42 can also be recessed in the support structure 38 to further electrically isolate it form other structures and for further mechanical protection.

Figure 7:
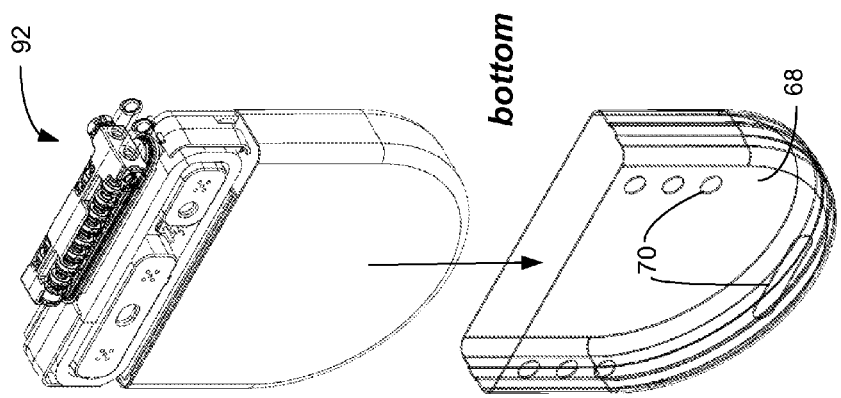
FIG. 7 shows positioning of a battery cover over the battery in the subassembly at another stage of construction.

Once IPG subassembly 92 has been constructed, it is removed from the jig 94, and a battery cover 68 is slipped over the battery 34, as shown in FIG. 7. The battery cover 68 typical comprises a thin plastic sleeve, and is used to electrically isolate the battery 34's case from the case 30 of the IPG 10, which may be at different potentials. The battery cover 68 includes at least one battery cover glue hole 70 through which the battery 34 can be adhered to the case 30 while still providing the desired electrical isolation.

The battery cover 68 may completely surround the battery 34, but as shown it only partially surrounds the battery 34, covering all surfaces of the battery 34 except the battery terminal face 57. However, the battery cover 68 is not limited, and other insulators may be used as well. For example, an insulative coating might be provided on the case of the battery 34, masked as necessary to form the glue holes 70 in the coating. Alternatively an insulating layer or sheet may be used that intervenes between the battery 34's case and the IPG case 30 where they come into contact or are close to doing so. This alternative of use of a single insulting layer or sheet might be a good option for use in the IPG 10, because as discussed further below with respect to FIGS. 10A and 10B, the battery 34 is affixed to the bottom side of the case 30 and an air gap "x" exists between the battery and the top side of the case, and thus an insulator may not be necessary on this side as the battery 34 and the case 30 are less likely to short by virtue of this air gap. The battery cover 68 or other insulator may also cover other portions of the IPG subassembly 92, such as the support structure to which the coil 40 and the PCB 42 are affixed to also prevent these structures from shorting to the case 30.

Figure 8:
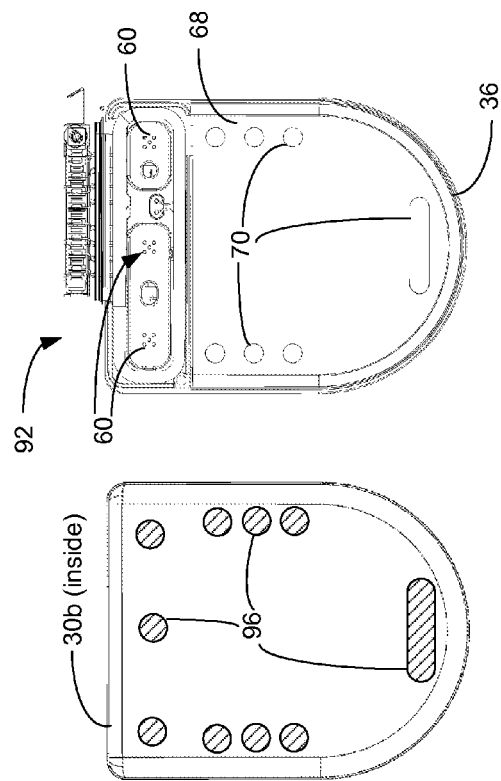
FIG. 8 shows placement of glue drops on an IPG case portion corresponding to locations of glue holes in the subassembly at another stage of construction.

As shown in FIG. 8, glue drops 96 are placed at multiple locations inside the bottom case portion 30b corresponding with the position of the support glue holes 60 in the support structure 38 and battery cover glue holes 70 in the battery cover 68. The IPG subassembly 92 is positioned in the bottom case portion 30b, as shown in FIG. 9, which causes the glue drops 96 to penetrate through the glue holes 70 in the battery cover 68 to come in contact with the battery 34, and through the glue holes 60 in the support structure 38, as further discussed below with respect to FIG. 10B. Alternatively, glue drops 96 could be placed on the IPG subassembly 92 at the holes 60 and 70, which is then positioned in the bottom case portion 30b. Glue drops 96 suitable for this application include NuSil™ Med3-4213 silicone, but other types of glues or other adhesives may be used as well. For example, double sided tape could be used in place of glue drops 96. The adhesive used at this step could comprise the same adhesive (58) used to affix the battery 34 to the support structure 38.

As further shown in FIG. 9, after the IPG subassembly 92 is affixed to the bottom case portion 30b via the glue drops 92, the top case portion 30a is positioned to surround at least part of the IPG assembly 92 (but not lead connector subassembly 95) in the case portions 30a and 30b, and to meet the feedthrough 32 at cutouts 62a and 62b (FIGS. 4A and 4B) in the case portions 30a and 30b. (Note that an applicator 66 (FIGS. 4A and 4B) is used as an aid to properly align the case). The case portions 30a and 30b are then preferably laser welded together and laser welded to the feedthrough 32, although other sealing methods could be used, such as brazing, or the use of hermitic glues or other adhesives.

Top and bottom case portions 30a and 30b with parallel top and bottom sides are not required, and instead the case 30 could comprise a uniform structure generally resembling a "cup" into which the subassembly 92 is placed and affixed. Such a cup-shaped case may also have parallel top and bottom sides. A cap, which may include the feedthrough 32, can then be welded to the open end of the cup.

Thereafter, the epoxy header 28 (FIG. 1) is affixed to the case 30 around the lead connectors 24 and the feedthrough 32 to from a hermetic seal in standard fashions, at which point construction of the IPG 10 is complete.

Figures 10A, 10B:
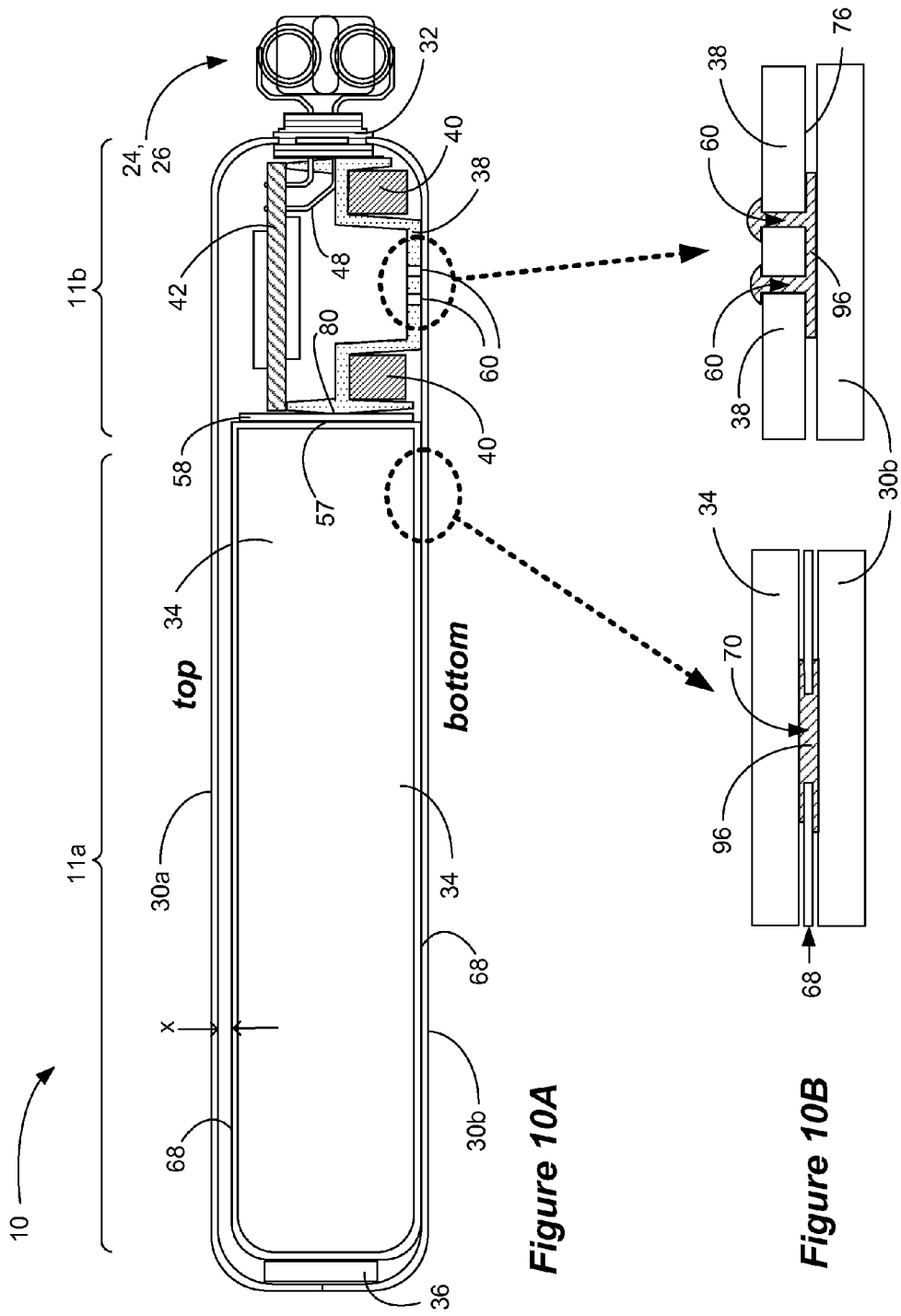
FIG. 10A shows cross sections of the completed IPG.
FIG. 10B shows the manner in which the glue drops adhere the battery and the support structure to the case.

FIG. 10A shows a cross section of the fully constructed IPG 10, which allows certain aspects and benefits of the design of the IPG to be appreciated. The bottom side of the battery 34 and the case contact surfaces 76 of the support structure 38 are planar and both are affixed to the bottom case portion 30b as is preferable to add mechanical robustness. However, this is not strictly necessary, and instead only one of the battery 34 and support structure 38 can be so affixed. Likewise, it is also not necessary that the bottom sides of the battery 34 and the case contact surfaces 76 of the support structure 38 are planar. Note the case contact surfaces 76 of the support structure 38 offset the coil 40 from the bottom case portion 30b to prevent short circuiting of the coil.

As shown, the relatively-large primary battery 34 occupies first area 11a in the case 30, while the support structure 38, coil 40, and PCB 42 occupy a second smaller area 11b in the case 30. The areas 11a and 11b preferably do not overlap. This is advantageous because the support structure 38, coil 40, and PCB 42 do not require the battery 34 to be thinned, as would occur if these structures overlapped. Because the battery 34 is not constrained by the thickness of these structures, the thickness of the battery 34 is allowed to substantially equal the thickness of the case 30 (e.g., within 15%). Coil 40 and PCB 42 are parallel and overlap each other in the second area 11b, and are parallel to the top and bottom sides of the case 30, and perpendicular to the battery terminal face 57 of the battery 34 and feedthrough 32. As shown, the support structure 38, coil 40, and PCB 42 can all be made to fit equal to or less than the thickness of the battery 34, which again does not constrain the thickness that the battery 34 can have inside the case 30. Although, this is not strictly necessary.

A small air gap "x" intervenes between the top side of the battery 34 and support structure 38 and the top case portion 30a, which is useful to protecting the battery 34 from heat during welding of the two case portions 30a and 30b. As a further protection against this heat, a back-up band 36 (not shown in FIG. 3) can be provided around the periphery of the IPG assembly 92, as best shown in FIG. 9. However, use of an air gap x is not strictly necessary. For example, the battery 34 could be affixed (e.g., glued) to both the top and bottom case portions 30a and 30b to leave no air gap, which would require battery cover glue holes 70 on both sides of the battery cover 68.

FIG. 10B is magnified illustration of the glue holes 70 in the battery cover 68 and the glue holes 60 in the case contact surfaces 76. Preferably enough glue 96 is provided to penetrate completely through the glue holes 60 to the other side of the support structure 38, thus creating a mushroom-shaped when dried, to anchor the support structure 38 to the bottom side case portion 30b. This preference though is not strictly necessary, and indeed the case contacts surfaces 76 can be glued or affixed to the bottom case portion 30b even if holes 60 are not present.

FIG. 10B also illustrates how glue 96 penetrates the glue holes 70 in the battery cover 68 to adhere the battery 34 to the bottom case portion 30b. Glue holes 70 are particularly advantageous in this case, because the material of the battery cover 68 is generally not suitable for adhesion. Because the material of the glue 96 is insulative, the battery 34 is affixed to the case 30 (despite the intervening battery cover 68) but is still electrically insulated therefrom, which as noted earlier is desired because they may be at different potentials.

It should be noted that the above construction steps are merely examples of how the IPG 10 as designed can be constructed, and other manners are also possible. For example, construction steps can occur in different orders, or involve different sub-steps or the consolidation of steps.

While the disclosed IPG design and method of construction were inspired by the use of larger primary batteries, the disclosed design and methods could also be used for an IPG having a rechargeable battery. In such a case, the IPG might have an additional antenna (not shown), such as another coil to wirelessly receive a charging field that is rectified to charge the battery. Such additional charging coil, like communication coil 40, could also be affixed to the disclosed support structure 38. Alternatively, the disclosed coil 40 could comprise a combined communication/charging coil capable of performing both communication and charging functions.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. An implantable medical device, comprising:
   a case;
   circuitry within the case configured to implement the functionality of the implantable medical device;
   a battery within the case electrically coupled to the circuitry;
   an insulating sleeve that surrounds at least a portion of the battery, wherein the insulating sleeve comprises at least one hole, and wherein the portion of the battery includes all surfaces of the battery other than the battery's terminal face; and
   a first adhesive, wherein the first adhesive affixes the battery to the case through the at least one hole, wherein the battery is electrically isolated from the case by the insulating sleeve and the first adhesive.

2. The device of claim 1, wherein the battery comprises a primary battery.

3. The device of claim 1, wherein the insulating sleeve comprises a plastic sleeve configured to slip over the battery.

4. The device of claim 1, wherein the first adhesive comprises glue.

5. The device of claim 1, wherein the case comprises first and second parallel sides, and wherein the battery is affixed to only the first side.

6. The device of claim 1, further comprising a support structure, wherein the battery is affixed to the support structure.

7. The device of claim 6, wherein the support structure is affixed to the battery by a second adhesive.

8. The device of claim 7, wherein the second adhesive comprises double sided tape.

9. The device of claim 6, wherein the battery is affixed to the support structure at the battery's terminal face.

10. The device of claim 6, wherein the support structure is affixed to the case.

11. The device of claim 10, wherein the case comprises first and second parallel sides, and wherein the battery and support structure are affixed to only the first side.

12. The device of claim 11, wherein there is an air gap between the battery and support structure and the second side.

13. The device of claim 6, wherein the circuitry is affixed to the support structure.

14. The device of claim 13, wherein the circuitry is integrated on a circuit board.

15. The device of claim 14, further comprising an antenna affixed to the support structure and electrically coupled to the circuit board.

16. The device of claim 15, wherein the antenna is recessed in the support structure.

17. The device of claim 15, wherein the antenna is electrically coupled to the circuit board by pins passing through the support structure.

18. The device of claim 15, wherein the antenna comprises a communication coil, a charging coil, or a combined communication and charging coil.

19. The device of claim 15, wherein the antenna and the circuit board are on opposite sides of the support structure.

20. The device of claim 15, wherein the antenna and the circuit board are parallel.

21. The device of claim 20, wherein the battery is affixed to the support structure at the battery's terminal face, and wherein the battery's terminal face is perpendicular to the antenna and the circuit board.

22. The device of claim 15, wherein the battery occupies a first area within the case, and wherein the support structure, circuit board, and antenna together occupy a second area of the case.

23. The device of claim 22, wherein the first and second areas do not overlap.

24. The device of claim 23, wherein the battery has a first thickness, and the support structure, circuit board, and antenna together comprise a second thickness equal to or less than the first thickness.

25. The device of claim 14, further comprising a plurality of feedthrough pins, wherein the feedthrough pins are electrically coupled to the circuit board.

26. The device of claim 25, further comprising a feedthrough coupled to the case for passing the feedthrough pins out of the case.

27. The device of claim 25, further comprising at least one lead connector external to the case comprising a plurality of electrode contacts, wherein the feedthrough pins are electrically coupled to the electrode contacts.

28. The device of claim 27, further comprising a header coupled to the case for enclosing the at least one lead connector.

* * * * *